(12) United States Patent
Rasselkorde et al.

(10) Patent No.: US 10,295,501 B2
(45) Date of Patent: May 21, 2019

(54) METHOD FOR ULTRASOUND SCANNING OF A WELD BUILDUP

(71) Applicant: Siemens Energy, Inc., Orlando, FL (US)

(72) Inventors: El Mahjoub Rasselkorde, Monroeville, PA (US); Michael F. Fair, Oakmont, PA (US); David S. Segletes, York, SC (US); Erik A. Lombardo, Sharon, SC (US); Scott M. Westby-Gibson, Charlotte, NC (US); Waheed A. Abbasi, Murrysville, PA (US)

(73) Assignee: SIEMENS ENERGY, INC., Orlando, FL (US)

( * ) Notice: Subject to any disclaimer, the term of this patent is extended or adjusted under 35 U.S.C. 154(b) by 1239 days.

(21) Appl. No.: 14/527,826

(22) Filed: Oct. 30, 2014

(65) Prior Publication Data

US 2016/0123932 A1 May 5, 2016

(51) Int. Cl.
| | |
|---|---|
| *G01N 29/11* | (2006.01) |
| *G01N 29/04* | (2006.01) |
| *F01D 21/00* | (2006.01) |
| *G01N 29/26* | (2006.01) |
| *G01N 29/27* | (2006.01) |
| *F01D 5/00* | (2006.01) |

(52) U.S. Cl.
CPC ........... *G01N 29/11* (2013.01); *F01D 21/003* (2013.01); *G01N 29/04* (2013.01); *G01N 29/262* (2013.01); *G01N 29/27* (2013.01); *F01D 5/005* (2013.01); *F05D 2220/31* (2013.01); *F05D 2230/232* (2013.01); *F05D 2230/80* (2013.01); *F05D 2260/80* (2013.01); *G01N 2291/106* (2013.01); *G01N 2291/267* (2013.01); *G01N 2291/2672* (2013.01); *G01N 2291/2693* (2013.01)

(58) Field of Classification Search
CPC ...... G01N 29/11; G01N 29/27; G01N 29/262; G01N 29/04; G01N 2291/267; G01N 2291/2693; F01D 21/003; F05D 2230/232
See application file for complete search history.

(56) References Cited

U.S. PATENT DOCUMENTS

| | | | |
|---|---|---|---|
| 8,839,673 B2 | 9/2014 | Rasselkorde et al. | |
| 2011/0109627 A1* | 5/2011 | Zhang | G01N 29/0654 345/420 |
| 2014/0200853 A1* | 7/2014 | Guan | G01N 29/069 702/189 |

\* cited by examiner

*Primary Examiner* — Regis J Betsch
*Assistant Examiner* — Jeremy A Delozier

(57) ABSTRACT

A method for scanning a weld buildup formed on a circumferential portion of a disc for a steam turbine. The method includes providing an ultrasound probe for generating at least one ultrasound beam sweep. The circumferential portion is scanned with a first beam sweep oriented in a first beam orientation to detect a first flaw type in the weld buildup. The circumferential portion is also scanned with a second beam sweep oriented in a second beam orientation to detect a second flaw type in the weld buildup. Further, the circumferential portion is scanned with a third beam sweep oriented in a third beam orientation to detect a third flaw type in the weld buildup. The method also includes rotating the disc about a disc axis during scanning of the circumferential portion and moving the first, second and third beam sweeps in a direction parallel to the disc axis during scanning.

21 Claims, 5 Drawing Sheets

METHOD FOR ULTRASOUND SCANNING OF A WELD BUILDUP

FIELD OF THE INVENTION

The invention relates to ultrasonic scanning of a weld buildup formed on a circumferential portion of a disc of a steam turbine, and more particularly, to a method for ultrasound scanning of the weld buildup that includes scanning the circumferential portion with first, second and third beam sweeps oriented in first, second and third beam orientations to detect first, second and third flaw types in the weld buildup.

BACKGROUND OF THE INVENTION

Components of a turbine, such as turbine rotors and discs, are subjected to high stresses due to high operational speeds and temperatures. This results in the erosion of material in areas in which a turbine blade is attached to a disc (i.e. turbine blade attachment areas) and in shaft coupling areas, for example, that have complex geometries. In order to reconstruct or repair eroded areas of the turbine, a weld buildup process is used. In this process, an area to be repaired undergoes an initial machining step to prepare the area for welding. Weld material is then welded to the repair area to form a weld buildup that is subsequently heat-treated. A final machining step is then performed in order to form a desired machined shape from the weld buildup. Prior to final machining, an ultrasonic inspection is performed in order to detect flaws in the weld buildup and determine the size of the flaws.

The ultrasonic inspection is performed manually using a conventional ultrasonic straight beam probe. However, this type of arrangement can only detect flaws that are oriented in a horizontal direction (i.e. 0 degrees). Therefore, it is desirable to provide improved flaw detection techniques in a turbine component.

SUMMARY OF INVENTION

Areas of a steam turbine disc such as a circumferential blade attachment area become eroded after continued operation of the turbine. The eroded area is repaired by welding material to the eroded area, which forms a weld buildup. An ultrasonic inspection is performed in order to detect flaws in the weld buildup and determine the size of the flaws. It has been found by the inventors herein that conventional ultrasonic inspection using an ultrasonic straight beam probe results in an inaccurate characterization of flaws in the weld buildup due to the beam spread of the probe. In particular, lab investigations of weld buildup test blocks show that flaws in the weld buildup may have orientations other than horizontal. In addition, flaws that are arranged in clusters are inaccurately characterized as linear flaws when using conventional ultrasonic inspection methods.

A method for scanning a weld buildup formed on a circumferential portion of a disc for a steam turbine is disclosed. The method includes providing an ultrasound probe for generating at least one ultrasound beam sweep. The circumferential portion is scanned with a first beam sweep oriented in a first beam orientation to detect a first flaw type in the weld buildup. The circumferential portion is also scanned with a second beam sweep oriented in a second beam orientation to detect a second flaw type in the weld buildup. Further, the circumferential portion is scanned with a third beam sweep oriented in a third beam orientation to detect a third flaw type in the weld buildup. The method also includes rotating the disc about a disc axis during scanning of the circumferential portion and moving the first, second and third beam sweeps in a direction parallel to the disc axis during scanning of the circumferential portion.

Those skilled in the art may apply the respective features of the present invention jointly or severally in any combination or sub-combination.

BRIEF DESCRIPTION OF DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
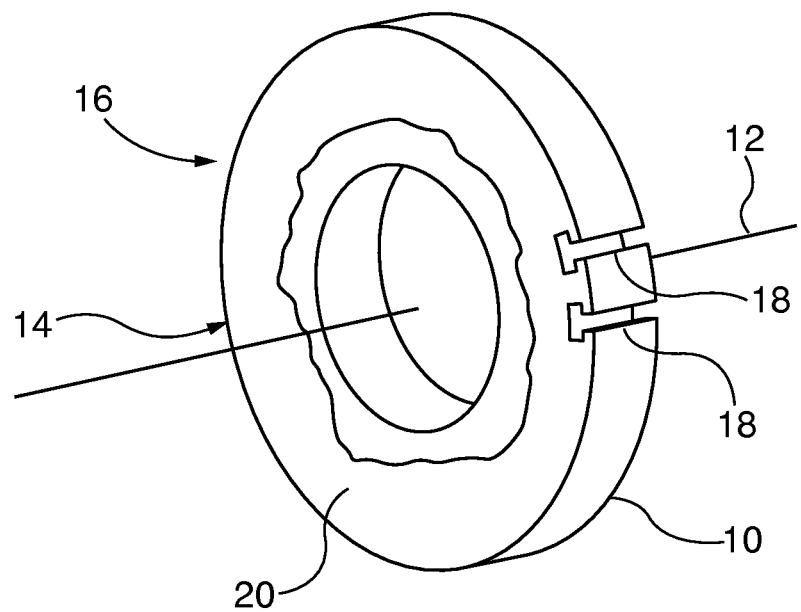
FIG. 1 is a view of an exemplary turbine disc of a steam turbine.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Referring to FIG. 1, a view of an exemplary turbine disc 10 of a steam turbine having a disc axis 12 is shown. It is understood that the current disclosure is also applicable to gas turbines and other types of turbines that have a weld buildup. The disc 10 includes a circumferential portion 14 having a turbine blade attachment area 16 including a plurality of channels or blade grooves 18 (only two grooves are shown in FIG. 1 for purposes of clarity) or other attachment features. Each groove 18 is adapted to receive a mating projecting portion of an associated turbine blade to thus attach the turbine blade to the disc 10. The turbine blade attachment area 16 becomes eroded as a result of operation of the turbine. In order to repair the blade attachment area 16, the circumferential portion 14 undergoes an initial machining step to prepare the area for welding. Weld material is then welded to the circumferential portion 14 to form a weld buildup 20 that is subsequently heat-treated. A final machining step is ultimately performed in order to form a desired machined shape from the weld buildup 20. Prior to final machining, an ultrasonic inspection is performed in order to detect flaws in the weld buildup 20 and determine the size of the flaws.

It has been found by the inventors herein that conventional ultrasonic inspection using an ultrasonic straight beam probe results in an inaccurate characterization of flaws in the weld buildup 20 due to the beam spread of the probe. In particular, lab investigations of weld buildup test blocks show that flaws in the weld buildup 20 may have orientations other than horizontal. In addition, flaws that are arranged in clusters are inaccurately characterized as linear flaws when using conventional ultrasonic inspection methods.

Figure 4:
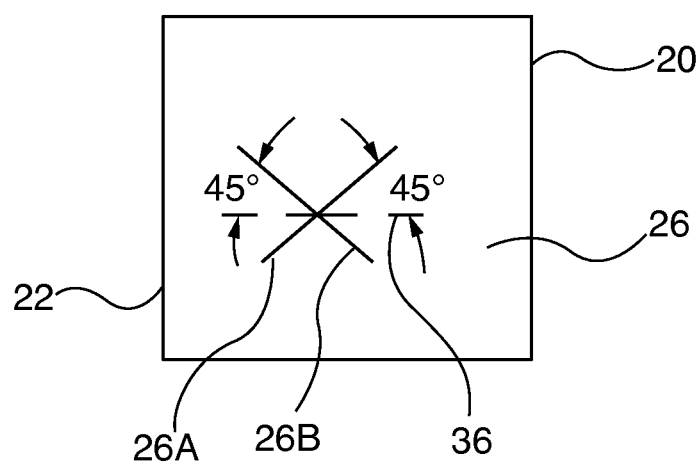
FIG. 4 is an end view of the disc along view line 4-4 of FIG. 2.
Figure 2:
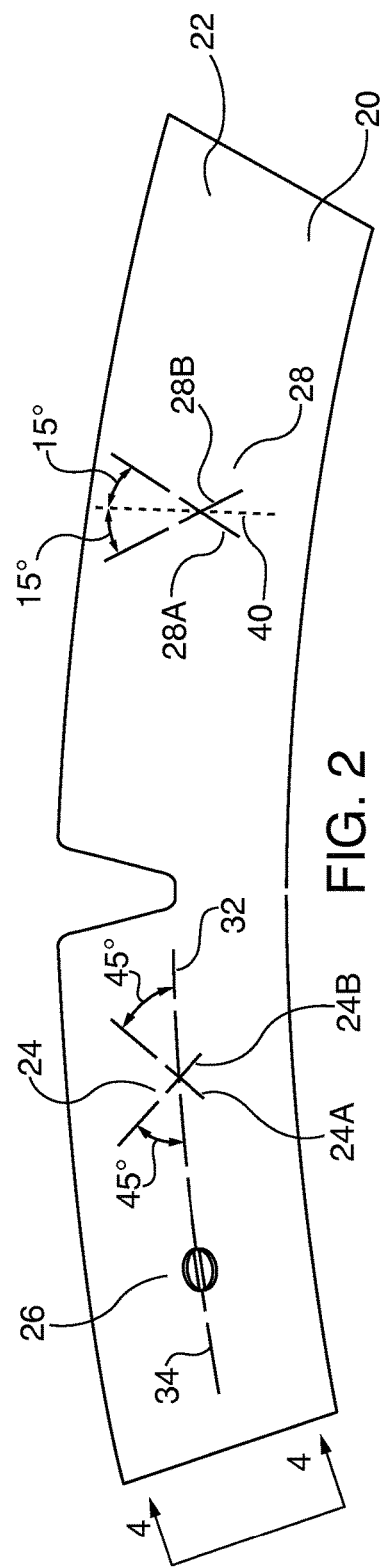
FIG. 2 is a side view of a section of the disc.
Figure 3:
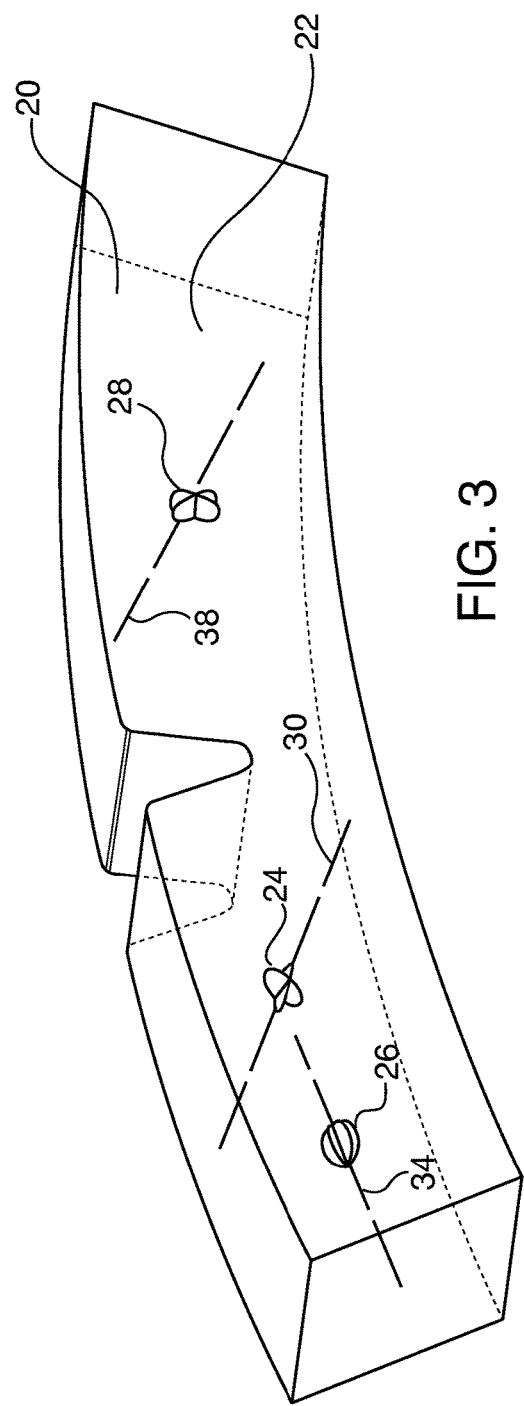
FIG. 3 is a perspective view of a section of the disc.

Referring to FIGS. 2 and 3, side and perspective views are shown of a section 22 of the disc 10. FIG. 4 is an end view of the disc 10 along view line 4-4 of FIG. 2. FIGS. 2, 3 and 4 depict possible first 24, second 26 and third 28 types of flaws that may occur in the weld buildup 20, as found by the inventors herein. A flaw in the weld buildup 20 may be categorized as either a first 24, second 26 or third 28 type of flaw based on an orientation of the flaw about an axis and its associated inclination angle. Referring to FIGS. 2 and 3, flaws categorized as a first flaw type 24 includes flaws that are oriented about an axial axis 30 (FIG. 3) and having an inclination angle of approximately ±45 degrees relative to a horizontal axis 32 (two exemplary flaw orientations 24A, 24B are shown in FIG. 2). Referring to FIG. 4 in conjunction with FIGS. 2 and 3, flaws categorized as a second flaw type 26 includes flaws that are oriented about a circumferential axis 34 (FIG. 3) and having an inclination angle of approximately ±45 degrees relative to a horizontal axis 36 (two exemplary flaw orientations 26A,26B are shown in FIG. 4). That is, the second flaw type 26 includes flaws that are oriented 90 degrees relative to the first flaw type 24. Referring back to FIGS. 2 and 3, flaws categorized as a third flaw type 28 includes flaws that are oriented about an axial axis 38 (FIG. 3) and having an inclination angle of approximately ±15 degrees relative to a vertical axis 40 (two exemplary flaw orientations 28A,28B are shown in FIG. 2).

The first 24 and second 26 flaw types are characterized as axial/circumferential flaws since the flaws 24,26 are generally oriented in a circumferential direction of the disc 10 (i.e. the flaws 24,26 are oriented approximately ±45 degrees relative to the horizontal axes 32,36, respectively). In addition, the third flaw type 28 is characterized as an axial/radial flaw since the flaw 28 is generally oriented in a radial direction (i.e. the flaw 28 is oriented approximately ±15 degrees relative to the vertical axis 40).

Figure 5:
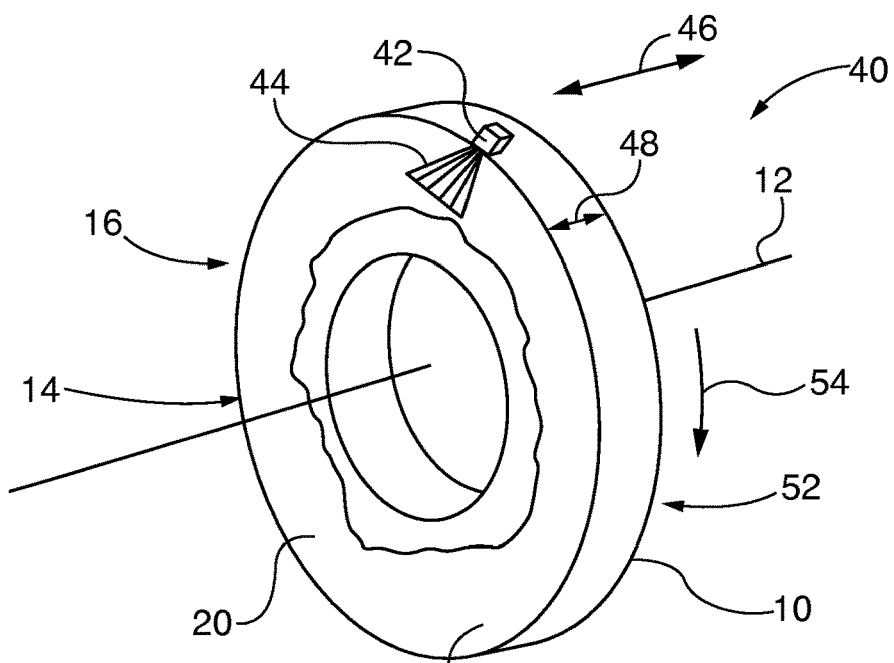
FIG. 5 depicts a first ultrasound scanning technique for detecting a first flaw type.

In accordance with the invention, first, second and third ultrasonic scanning techniques are used to detect the first 24, second 26 or third 28 flaw types, respectively. Referring to FIG. 5, a first ultrasound scanning technique 40 for detecting the first flaw type 24 is shown. An ultrasonic phased array system having a multi element probe 42 is used in the scanning techniques. The probe 42 generates a longitudinal wave (i.e. L-wave) that extends downward toward the disc axis 12 and through the circumferential portion 14 of the disc 10. In particular, the probe 42 generates an ultrasound beam that sweeps in a direction substantially perpendicular to the disc axis 12 to form a beam sweep 44 that is transverse to the disc axis 12. The probe 42 is also moved in an axial direction 46 substantially parallel to the disc axis 12 such that the transverse beam sweep 44 moves through a width 48 of the disc 10 between first 50 and second 52 sidewalls of the circumferential portion 14. Further, the disc 10 simultaneously rotates in a selected direction 54 (i.e. either a clockwise or counterclockwise direction) about the disc axis 12 as the probe 42 is moved in the axial direction 48 to form an L-wave radial scan.

Figure 6:
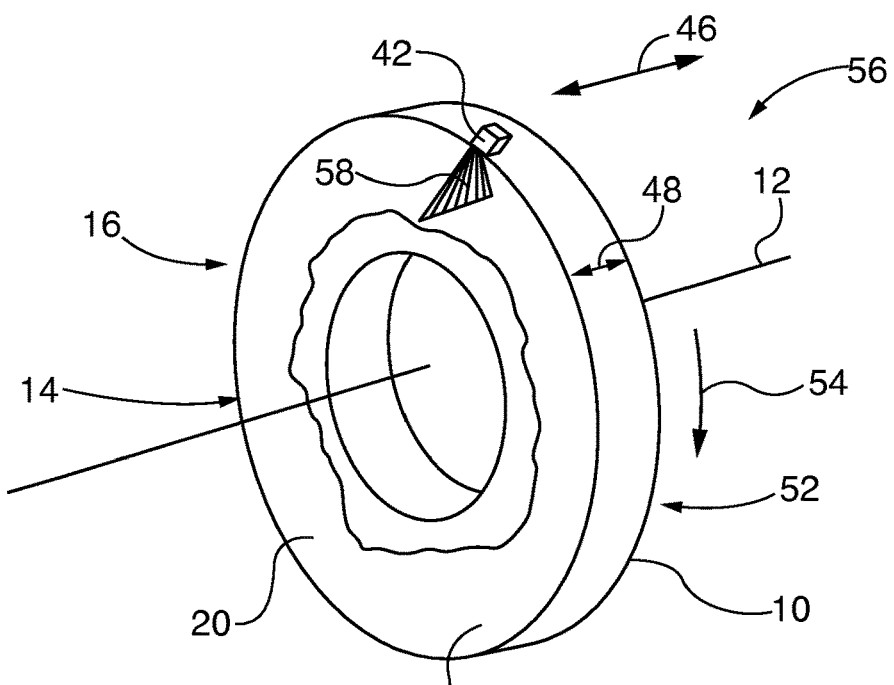
FIG. 6 depicts a second ultrasound scanning technique for detecting a second flaw type.

Referring to FIG. 6, a second ultrasound scanning technique 56 for detecting the second flaw type 26 is shown. The probe 42 generates a longitudinal wave (i.e. L-wave) that extends downward toward the disc axis 12 and through the circumferential portion 14 of the disc 10. In the second scanning technique 56, the probe 42 generates an ultrasound beam that sweeps in a direction substantially parallel to the disc axis 12 to form a beam sweep 58 that is aligned with the disc axis 12. The 42 probe is also moved in the axial direction 46 such that the aligned beam sweep 58 moves through the disc width 48 between the first 50 and second 52 sidewalls of the circumferential portion 14. Further, the disc 10 simultaneously rotates in a selected direction 54 (i.e. either a clockwise or counterclockwise direction) about the disc axis 12 as the probe 42 is moved in the axial direction 48 to form an L-wave axial scan. In the first 40 and second 52 scanning techniques, the ultrasound beam may sweep an angle that ranges between ±40 degrees in increments of 4 degrees, for example.

Figure 7:
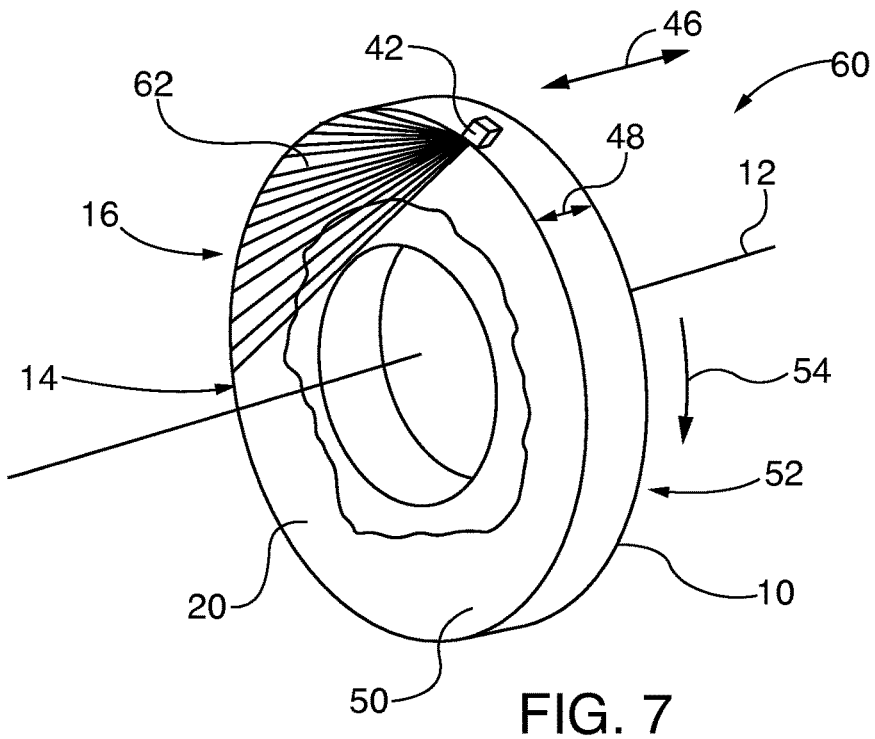
FIG. 7 depicts a third ultrasound scanning technique for detecting a third flaw type.

Referring to FIG. 7, a third ultrasound scanning technique 60 for detecting the third flaw type 28 is shown. The probe 42 generates a shear wave (i.e. S-wave) that extends in a circumferential direction and through the circumferential portion 14 of the disc 10. In the third scanning technique 60, the probe 42 generates an ultrasound beam that sweeps in a direction substantially perpendicular to the disc axis 12 to form a beam sweep 62 that is transverse to the disc axis 12. The probe 42 is also moved in the axial direction 46 such that the transverse beam sweep 62 moves through the disc width 48 between first 50 and second 52 sidewalls of the circumferential portion 14. Further, the disc 10 simultaneously rotates in a selected direction 54 (i.e. either a clockwise or counterclockwise direction) about the disc axis 12 as the probe 42 is moved in the axial direction 48 to form an S-wave tangential scan. In this embodiment, the sweep angle depends on the outer diameter and the width of the disc but may vary from approximately 35 degrees to a maximum of approximately 89 degrees. The probe 42 used in the first 40 and second 56 scanning techniques may be a phased array probe operating at a frequency of 5 MHz such as those sold by Imasonic. Probe 42 used in the third scanning technique 60 may be a phased array probe operating at a frequency of 4 MHz such as that sold by Olympus NDT.

The first 40, second 56 and third 60 scanning techniques provide information that is used to generate a visual representation of a flaw indication, or more than one flaw indication, that may exist in the weld buildup 20. In particular, each flaw indication may correspond to a single flaw or a cluster of flaws. A known flaw sizing method such as a distance-gain-size (i.e. DGS) method is used to determine whether a detected flaw indication exceeds a predetermined size threshold. If the threshold is met, a probe having a higher resolution is then used in order to characterize the flaw as a single flaw or a cluster of flaws, for example. In an embodiment, a phased array probe that operates at a frequency of 10 MHz, such as that sold by Imasonic, may be used in order to provide greater resolution.

Figure 8:
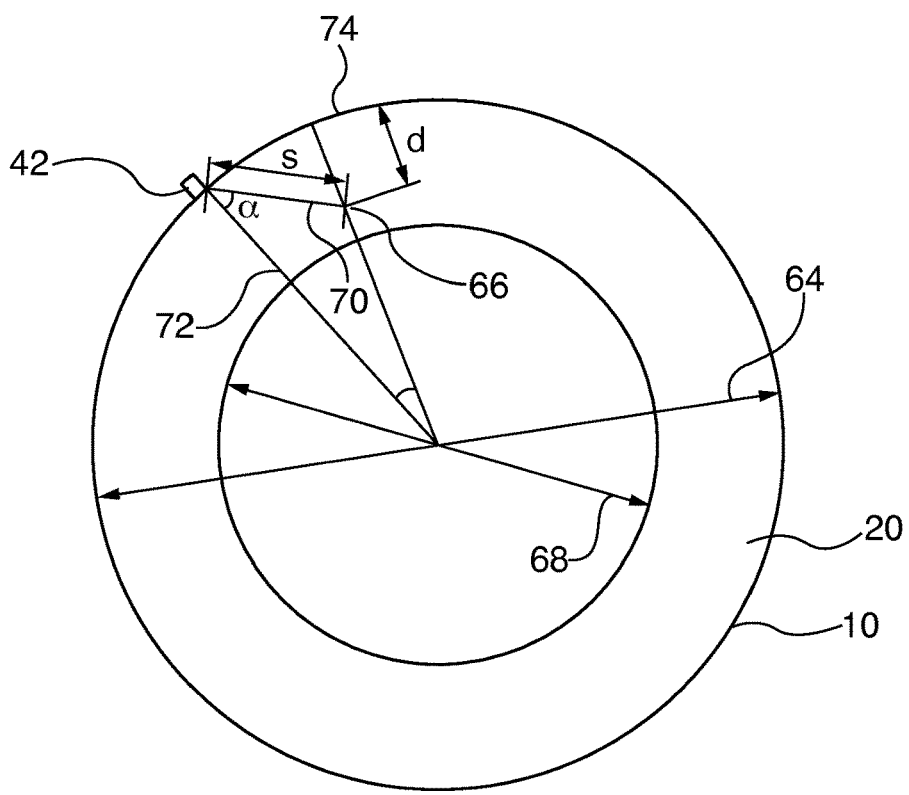
FIG. 8 is a side view of the disc.

The weld buildup 20 may have different configurations based on the amount of weld material that is used. Referring to FIG. 8, a side view of the disc 10 is shown. An outer diameter 64 of the disc 10 may be between approximately 304.8 mm to 3048 mm and a disc width 48 (see FIG. 5) may be between approximately 25 min to 330 mm due to a weld buildup. Further, a maximum thickness of the weld buildup 20 on disc 10 is approximately 127 mm. A scan plan is used to provide a methodology for conducting ultrasound scanning of the disc 10. The scan plan includes the calculation of a distance (i.e. a sound path) from the probe 42 to a flaw 66 given by the following equation $$s = \frac{1}{2}\left(OD \cdot \cos(\alpha) - \sqrt{ID^2 - OD^2 \cdot \sin^2(\alpha)}\right) \quad (1)$$

where s is the sound path, OD is the outer diameter 64, ID is an inner diameter 68 of the disc 10 and $\alpha$ is an angle between a path 70 of an ultrasound beam emitted by the probe 42 and an outer radius 72 of the disc 10. The sound path provides information to an operator of ultrasound equipment as to where (in terms of sound path or time of flight) to expect a reflection from a flaw. This enables adjustment of the sound path by the operator so as to able receive a reflection from a flaw. Further, the sound path equation enables determination of the beam angles needed to detect the first 24, second 26 and third 28 flaw types.

Further, a depth of a flaw may be determined by the following equation:

$$d = \frac{1}{2}\left(OD - \sqrt{OD^2 + 4 \cdot s^2 - 4 \cdot OD \cdot s \cdot \cos(\alpha)}\right) \quad (2)$$

where d is a distance between an outer surface 74 of the disc 10 and the flaw 66 (i.e. flaw depth), OD is the outer diameter 64, ID is the inner diameter 68. $\alpha$ is the angle between the path 70 of the ultrasound beam emitted by probe 42 and the outer radius 72 and s is the sound path calculated in equation (1). It is noted that the current invention is applicable to weld buildups formed in other areas of a turbine such as in shaft coupling areas wherein a disc is attached to a rotor shaft.

Figure 9:
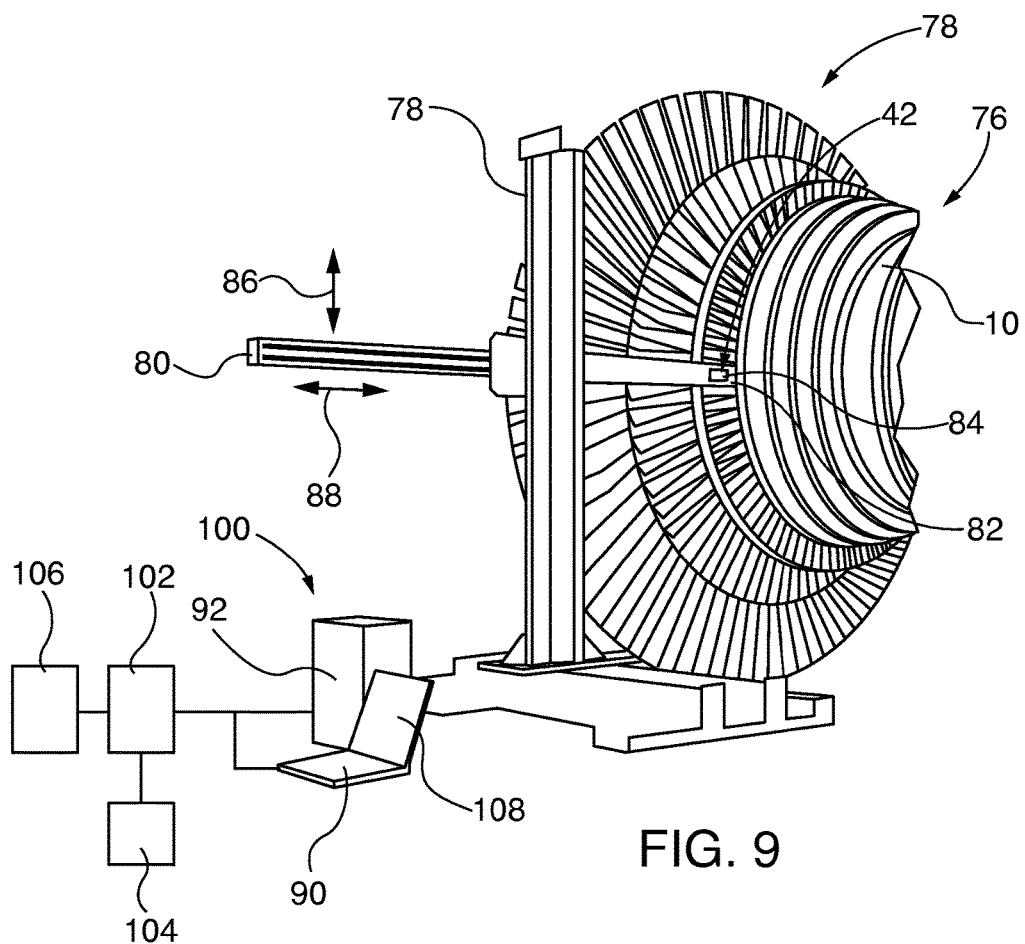
FIG. 9 is a view of an ultrasound inspection system in accordance with the present invention.

Referring to FIG. 9, an ultrasound inspection system 76 in accordance with the present invention is shown. The system 76 is used to scan the weld buildup 20 formed the disc 10 (see FIG. 1). In FIG. 9, a plurality of different size discs 10 is shown with turbine blades 78 installed. The system 76 includes a vertical stand 78 and a horizontal arm 80 that extends toward a disc 10. An end 82 of the arm 80 includes a holder 84 for holding the probe 42. The arm 80 is moveable in vertical 86 and horizontal 88 directions relative to the stand 78 to enable placement of the probe 42 in a position that is suitable for performing the first 40, second 56 and third 60 scanning techniques. The system 76 also includes an ultrasonic inspection analyzer 100 that is communicatively coupled to the probe 42 by known means such as cables. Ultrasound scanning data obtained by the probe 42 is routed to the analyzer 100. The analyzer 100 may include a general purpose computer 90 having software for controlling a controller 92 that is used to generate the ultrasound scans. During scanning, the probe 42 is stationary and the disc 10 rotates relative to the probe 42. Alternatively, the disc 10 is stationary and the probe 42 is configured to move around the disc 10 circumference during scanning.

The analyzer 100 may be a dedicated electronic device, such as a DYNARAY® Phased Array instrument from Zetec, Inc. of Snoquahnie, Wash., USA and/or the computer 90 and controller 92. Either type device preferably has a processor 102 including software instruction modules 104 stored in memory 106 that when executed by the processor 102 correlate scanned waveform data sets with position and size of flaws within the weld buildup 20 by means of DGS correlation methods. The analyzer 100 utilizes data acquisition and visualization software such as UltraVision® 3 data acquisition and visualization software supplied by Zetec, Inc. Flaw or discontinuity information is available for operator inspection at human machine interface 108 that may include any combination of visual display, touch screen, smart tablet, smart phone, keypad or keyboard, mouse or other known pointing device.

It is also to be understood that the present invention analyzer 100 may be implemented in various forms of hardware, software, firmware, special purpose processors, or a combination thereof. Preferably, as noted above, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device, or as also noted above a human machine interface. Further, the entire disclosure of U.S. Pat. No. 8,839,673, issued on Sep. 23, 2014 and entitled SYSTEM AND METHOD FOR INDUSTRIAL ULTRASONIC INSPECTION USING PHASED ARRAY PROBE AND DISTANCE-GAIN-SIZE FLAW SIZING, is hereby incorporated by reference in its entirety.

Figure 10:
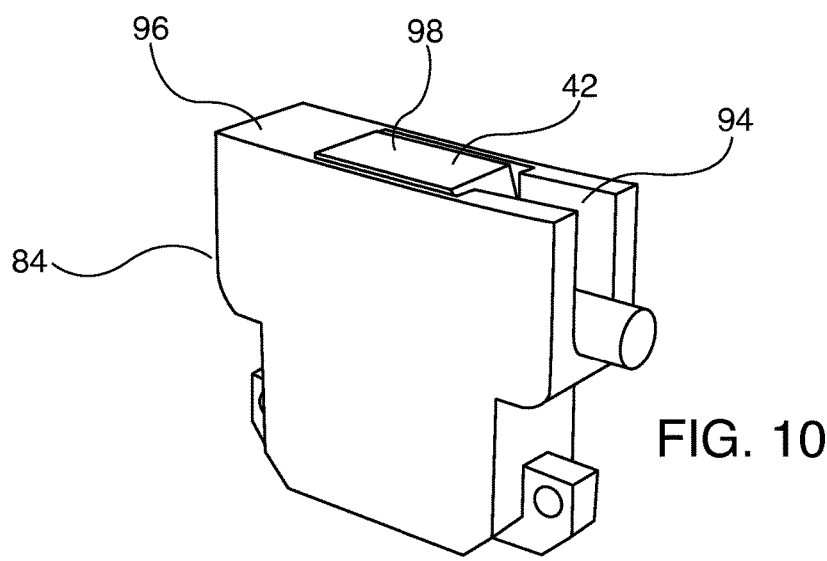
FIG. 10 is a view of a holder for holding an ultrasound probe.

Referring to FIG. 10, the holder 84 for holding the probe 42 is shown. The holder 84 includes a channel 94 that extends through an outer surface 96 of the holder 84. The probe 42 is located in the channel 94 such that a surface 98 of the probe 42 is exposed.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for scanning a weld buildup formed on a circumferential portion of a disc for a turbine wherein the disc is oriented about a disc axis, comprising:
   providing an ultrasound probe for generating at least one ultrasound beam sweep;
   scanning the circumferential portion with a first beam sweep oriented in a first beam orientation to detect a first flaw type in the weld buildup;
   scanning the circumferential portion with a second beam sweep oriented in a second beam orientation to detect a second flaw type in the weld buildup;

scanning the circumferential portion with a third beam sweep oriented in a third beam orientation to detect a third flaw type in the weld buildup;

rotating the disc about the disc axis during scanning of the circumferential portion; and moving the first, second and third beam sweeps in a direction parallel to the disc axis during scanning of the circumferential portion;

utilizing, by a processor communicatively coupled to the ultrasound probe, the detected flaw data to determine the position and size of a flaw within the weld buildup; and displaying the determined position and size of the flaw within the weld buildup via a visual display.

2. The method according to claim 1, wherein the first beam orientation is transverse to the disc axis and directed toward the disc axis.

3. The method according to claim 1, wherein the second beam orientation is aligned with the disc axis and directed toward the disc axis.

4. The method according to claim 1, wherein the third beam orientation is transverse to the disc axis and directed in a tangential direction relative to the circumferential portion.

5. The method according to claim 1, wherein the first flaw type is oriented about an axial axis and has an inclination angle of approximately ±45 degrees relative to a horizontal axis.

6. The method according to claim 1, wherein the second flaw type is oriented about a circumferential axis and has an inclination angle of approximately ±45 degrees relative to a horizontal axis.

7. The method according to claim 1, wherein the third flaw type is oriented about an axial axis and has an inclination angle of approximately ±15 degrees relative to a vertical axis.

8. The method according to claim 1, wherein the first and second beam sweeps include a longitudinal wave.

9. The method according to claim 1, wherein the third beam sweep includes a shear wave.

10. The method according to claim 1, wherein an angle of the first and second beam sweeps is approximately ±40 degrees.

11. The method according to claim 1, wherein an angle of the third beam sweep is approximately 35 degrees to 89 degrees.

12. A method for scanning a weld buildup formed on a circumferential portion of a disc for a turbine wherein the disc is oriented about a disc axis, comprising:

providing an ultrasound probe for generating at least one ultrasound beam sweep;

scanning the circumferential portion with a first beam sweep oriented in a first direction toward a disc axis to detect a first flaw type in the weld buildup;

scanning the circumferential portion with a second beam sweep oriented in a second beam orientation transverse to the first beam sweep and toward the disc axis to detect a second flaw type in the weld buildup;

scanning the circumferential portion with a third beam sweep oriented in a third direction tangential to the circumferential portion to detect a third flaw type in the weld buildup;

rotating the disc about the disc axis during scanning of the circumferential portion; and moving the first, second and third beam sweeps in a direction parallel to the disc axis during scanning of the circumferential portion;

utilizing, by a processor communicatively coupled to the ultrasound probe, the detected flaw data to determine the position and size of a flaw within the weld buildup; and displaying the determined position and size of the flaw within the weld buildup via a visual display.

13. The method according to claim 12, wherein the first beam sweep is transverse to the disc axis.

14. The method according to claim 12, wherein the second beam sweep is aligned with the disc axis.

15. The method according to claim 12, wherein the third beam sweep is transverse to the disc axis.

16. The method according to claim 12, wherein the first flaw type is oriented about an axial axis and has an inclination angle of approximately ±45 degrees relative to a horizontal axis.

17. The method according to claim 12, wherein the second flaw type is oriented about a circumferential axis and has an inclination angle of approximately ±45 degrees relative to a horizontal axis.

18. The method according to claim 12, wherein the third flaw type is oriented about an axial axis and has an inclination angle of approximately ±15 degrees relative to a vertical axis.

19. A method for scanning a weld buildup formed on a circumferential portion of a disc for a turbine wherein the disc is oriented about a disc axis, comprising:

providing an ultrasound probe for generating at least one ultrasound beam sweep;

scanning the circumferential portion with a first beam sweep oriented in a first beam orientation to detect a first flaw type in the weld buildup;

scanning the circumferential portion with a second beam sweep oriented in a second beam orientation to detect a second flaw type in the weld buildup;

scanning the circumferential portion with a third beam sweep oriented in a third beam orientation to detect a third flaw type in the weld buildup;

rotating the disc about the disc axis during scanning of the circumferential portion;

moving the first, second and third beam sweeps in a direction parallel to the disc axis during scanning of the circumferential portion;

calculating a sound path between the probe and a flaw; and calculating a depth of the flaw;

utilizing, by a processor communicatively coupled to the ultrasound probe, the detected flaw data and the depth of the flaw to determine the position and size of a flaw within the weld buildup; and displaying the determined position and size of the faw within the weld buildup via a visual display.

20. The method according to claim 19, wherein the sound path is calculated by:

$$s = \tfrac{1}{2}(OD \cdot \cos(\alpha) - \sqrt{ID^2 - OD^2 \cdot \sin^2(\alpha)})$$

where s is the sound path, OD is the outer diameter of the disc, ID is an inner diameter of the disc and $\alpha$ is an angle between a path of an ultrasound beam emitted by the probe and an outer radius of the disc.

21. The method according to claim 19, wherein the depth is calculated by:

$$d = \tfrac{1}{2}(OD - \sqrt{OD^2 + 4 \cdot s^2 - 4 \cdot OD \cdot s \cdot \cos(\alpha)})$$

where d is a distance between an outer surface of the disc and a flaw 66, OD is an outer diameter of the disc, ID is an inner diameter of the disc and $\alpha$ is an angle between a path of an ultrasound beam emitted by the probe and an outer radius of the disc.

* * * * *